United States Patent
Hasegawa

(10) Patent No.: US 9,232,925 B2
(45) Date of Patent: Jan. 12, 2016

(54) X-RAY DIAGNOSTIC APPARATUS AND STORAGE MEDIUM STORING X-RAY DIAGNOSTIC PROGRAM

(75) Inventor: Naoki Hasegawa, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 110 days.

(21) Appl. No.: 14/113,176

(22) PCT Filed: Apr. 22, 2011

(86) PCT No.: PCT/JP2011/002377
§ 371 (c)(1),
(2), (4) Date: Oct. 21, 2013

(87) PCT Pub. No.: WO2012/143979
PCT Pub. Date: Oct. 26, 2012

(65) Prior Publication Data
US 2014/0086472 A1 Mar. 27, 2014

(51) Int. Cl.
*G06K 9/00* (2006.01)
*A61B 6/00* (2006.01)
*G06T 5/00* (2006.01)
*G06T 5/20* (2006.01)
*G06T 7/00* (2006.01)
*G06T 5/10* (2006.01)

(52) U.S. Cl.
CPC .............. *A61B 6/4291* (2013.01); *A61B 6/5258* (2013.01); *G06T 5/002* (2013.01); *G06T 5/10* (2013.01); *G06T 5/20* (2013.01); *G06T 7/0012* (2013.01); *A61B 6/5205* (2013.01); *A61B 6/5282* (2013.01); *G06T 2207/10116* (2013.01); *G06T 2207/20012* (2013.01); *G06T 2207/20056* (2013.01); *G06T 2207/20224* (2013.01)

(58) Field of Classification Search
None
See application file for complete search history.

(56) References Cited

U.S. PATENT DOCUMENTS

| 5,771,308 A * | 6/1998 | Florent ........................ 382/130 |
| 2002/0024027 A1 | 2/2002 | Yamada |
| 2005/0031182 A1* | 2/2005 | Inoue ..................... G06T 5/002 382/132 |
| 2010/0034441 A1* | 2/2010 | Makram-Ebeid ...... A61B 6/481 382/128 |

FOREIGN PATENT DOCUMENTS

| JP | 2002-152467 A | 5/2002 |
| JP | 2005-052553 A | 3/2005 |
| JP | 2010-240259 A | 10/2010 |

OTHER PUBLICATIONS

International Search Report, w/ English translation thereof, issued in International Application No. PCT/JP2011/002377 dated May 31, 2011.

\* cited by examiner

*Primary Examiner* — Utpal Shah
*Assistant Examiner* — Mai Tran
(74) *Attorney, Agent, or Firm* — McDermott Will & Emery LLP

(57) ABSTRACT

An X-ray diagnostic apparatus includes a peak frequency detector detecting a peak frequency of a first harmonic in a moiré pattern of a grid in an image; a harmonic remover removing the first harmonic and a second harmonic in the moiré pattern from the image in accordance with the peak frequency of the first harmonic to obtain a first and second harmonic removed image; a harmonic extracting-filter generating unit calculating a peak frequency of a third harmonic in the moiré pattern in accordance with the peak frequency of the first harmonic to generate a harmonic extracting filter to extract the third harmonic; a harmonic extracting unit extracting the third harmonic from the first and second harmonic removed image based on the harmonic extracting filter; and a harmonic subtracting unit subtracting the extracted third harmonic from the first and second harmonic removed image to obtain a third harmonic removed image.

20 Claims, 11 Drawing Sheets

Fig. 5
(a)
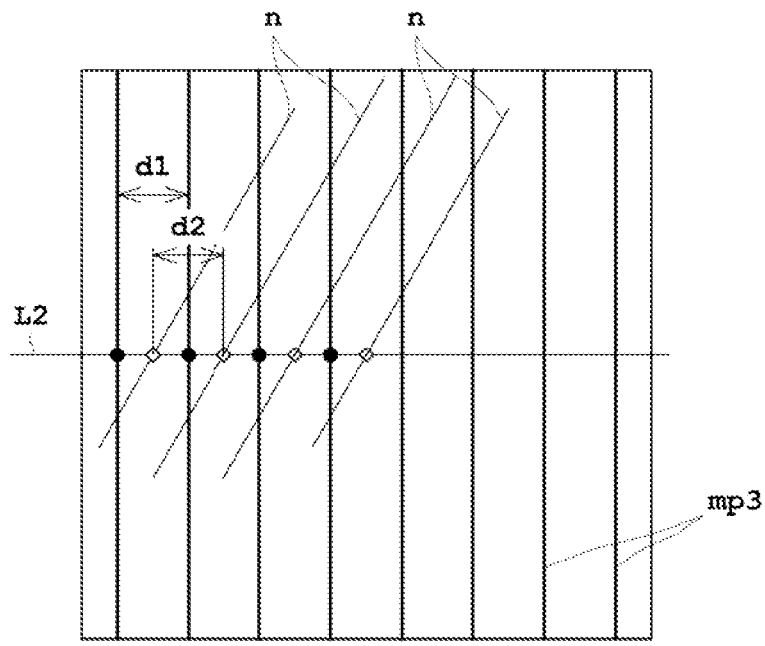
(b)
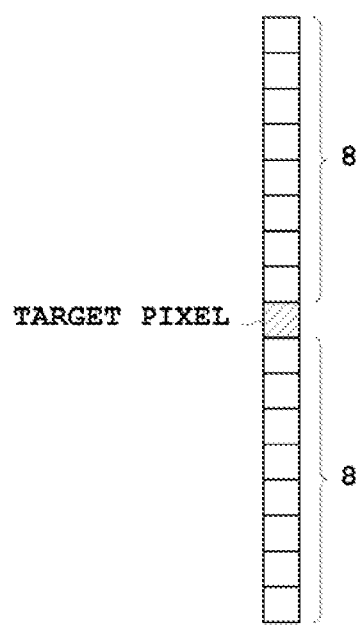

X-RAY DIAGNOSTIC APPARATUS AND STORAGE MEDIUM STORING X-RAY DIAGNOSTIC PROGRAM

RELATED APPLICATIONS

This application is the U.S. National Phase under 35 U.S.C. §371 of International Application No. PCT/JP2011/002377, filed on Apr. 22, 2011, the disclosure of which Application is incorporated by reference herein.

TECHNICAL FIELD

The present invention relates to an X-ray diagnostic apparatus and a storage medium storing an X-ray diagnostic program to remove a moiré pattern of a grid appearing in an X-ray image.

BACKGROUND ART

As illustrated in FIG. 11, a conventional X-ray diagnostic apparatus includes an X-ray tube 103 that irradiates a subject M with X-rays; an X-ray detector (e.g., a flat panel X-ray detector (FPD)) 104 that detects X-rays transmitting through the subject M; and a scattered-radiation removal grid (hereinunder, abbreviated as "grid") 105 disposed on a side where X-rays enter into the X-ray detector 104. The grid 105 removes X-rays scattered upon transmitting through the subject M. The grid 105 is formed by absorbers (e.g., lead) and transmission elements (e.g., aluminum or air) arranged alternately, the absorbers absorbing X-rays and the transmission elements transmitting X-rays. In the grid 105, the absorbers absorb X-rays scattered and entering obliquely, and the X-ray detector 104 only detects X-rays transmitting through the transmission elements. This enables to obtain a clear image.

In the conventional X-ray diagnostic apparatus 101, however, a moiré pattern of the grid 105 appears in the obtained image due to difference between resolution of the X-ray detector 104 and density of the grid 105. Such a problem may arise. Various suggestions have been made to take measures against the moiré pattern of the grid 105. See, for example, Japanese Patent Publication No. 2002-152467A.

Moreover, the conventional X-ray diagnostic apparatus 101 as illustrated in FIG. 11 includes a moiré pattern remover 121. The moiré pattern remover 121 removes a first harmonic and a second harmonic in the moiré pattern of the grid 105 appearing in the image. First, one-dimensional Fourier transform is performed to the image with the moiré pattern appearing therein. Then, in accordance with results from the Fourier transform, a peak frequency representing the first harmonic in the moiré pattern is detected. Here, the second harmonic is twice (integral multiple) the first harmonic, and thus enables to be calculated from the peak frequency of the first harmonic. Then, in accordance with the peak frequencies of the obtained first and second harmonics, a filter is prepared to extract the first and second harmonics in the moiré pattern. The first and second harmonics are extracted using the filter. Thereafter, the first and second harmonics are subtracted from the image with the moiré pattern appearing therein. As a result, the first and second harmonics in the moiré pattern are removed.

The resolution of the X-ray detector 104 enables to be expressed by a Nyquist frequency Ny. Here, a Nyquist frequency Ny represents a limit of spatial frequencies that enables to be sampled at pixel pitches δ (mm). The Nyquist frequency Ny is calculated from Equation (1) as under:

$$Ny=1/(2\times\delta) \quad (1)$$

For instance, assuming that the X-ray detector 104 has pixel pitches δ of 150 μm, a Nyquist frequency Ny is calculated:

$$Ny=1/(2\times 0.15)=3.33\ldots \text{lp/mm}.$$

That is, the resolution of the X-ray detector 104 is 3.33 . . . lp/mm. Here, the resolution of the X-ray detector 104 is appropriately assumed to be "3.33 lp/mm".

Moreover, the density of the grid 105 is, for example, 50 line/cm. Here, 50 line/cm is also expressed by 5 line/mm or 5 lp/mm. As for the grid 105, "line/cm" or "lp/mm" represents the number of absorbers or the number of pairs of the absorber and transmission element (e.g., 50 or 5) per unit of length (e.g., 1 cm or 1 mm). When the X-ray detector with the resolution of 3.33 lp/mm and the grid with the density of 5 lp/mm (50 line/cm) are used, a moiré pattern of the grid (5 lp/mm) is folded at 3.33 lp/mm and thus occurs in a position of 1.67 lp/mm. In other words, a first harmonic in the moiré pattern of the grid appears in a position of 3.33 . . . lp/mm−(5 lp/mm−3.33 . . . lp/mm)=1.67 (1.666 . . . ) lp/mm.

SUMMARY OF INVENTION

Technical Problem

The conventional X-ray diagnostic apparatus 101 having such a configuration, however, possesses the following problem. Although the moiré pattern remover 121 removes the moiré pattern of the grid 105 from the image having the moiré pattern appearing therein, the image having undergone removing process may contain a remaining moiré pattern.

The present invention has been made regarding the state of the art noted above, and its object is to provide an X-ray diagnostic apparatus and a storage medium storing an X-ray diagnostic program to remove a moiré pattern remaining in a moiré-pattern removed image.

Solution to Problem

To fulfill the above object, Inventor has made intensive research and attained the following findings. It has been proved that a moiré pattern remaining in a moiré-pattern removed image corresponds to a third harmonic. FIG. 13 illustrates one example of one-dimensional Fourier transform performed to an image. Specifically, a grid 105 of 50 line/cm is used for an X-ray detector (FPD) 104 having pixel pitches of 150 μm. In FIG. 13, the first harmonic in a moiré pattern of the grid 105 has the peak frequency of approximately 1.84 lp/mm, and the second harmonic has the peak frequency of approximately 2.98 lp/mm. A frequency component exists having a peak frequency of approximately 1.14 lp/mm. This frequency component corresponds to the third harmonic. That is, the third harmonic has a frequency of 5.52 lp/mm. The frequency is three times (integral multiple) the frequency of the first harmonic. The frequency of 5.52 lp/mm is folded at the frequency of 3.33 lp/mm and appears at a frequency of 1.14 lp/mm. Here, the second harmonic has a frequency of 3.68 lp/mm, the frequency being twice the frequency of the first harmonic, and is folded to appear at a frequency of 2.98 lp/mm.

It has also been proved that errors in density of the grid 105 lead to generation of the third harmonic in the moiré pattern in the image with the moiré pattern being already removed therefrom. For instance, the grid has a density of 50 line/cm and partially of 45 to 55 line/cm. This is because the grid 105 has a tolerance of the grid density within a range of ±10% that is allowable in Japanese Industrial Standard (JIS).

FIG. 14 illustrates a relationship between a grid error and peak frequencies of the harmonics in the moiré pattern. Specifically, as illustrated in FIG. 14, a longitudinal axis represents peak frequencies (lp/mm) of the first to third harmonics, and a horizontal axis represents a ratio of a grid of 50 line/cm to a grid with errors actually. For instance, where the actual grid density is 51 line/cm, a grid error (ratio) is 51/50=1.02. It is assumed that the X-ray detector (FPD) 104 has a pixel pitch of 150 μm. Note that in the moiré pattern illustrated in FIG. 13 mentioned above, the actual grid density is 48.2 line/cm, and thus the grid error (ratio) is 48.2/50=0.96 (denoted by numeral E). In FIG. 14, where the grid 105 of 50 line/cm has no error in the number of lines (denoted by numeral R), the first harmonic substantially overlaps the third harmonic. Accordingly, removal of the first harmonic causes the third harmonic to be removed simultaneously. Where an error exists in the grid density, deviation in peak frequency occurs between the first and third harmonics. As a result, the third frequency of the moiré pattern remains in the image after removal.

Moreover, when the first and second harmonics in the moiré pattern are removed and the third harmonic is further removed, many pieces of information in the image are to be removed simultaneously. Consequently, when only the third harmonic is removed, visibility of the image degrades that expresses clear recognition of an image (a subject in an image). As illustrated in FIGS. 13 and 14, when the third harmonic on a lower frequency side is removed, for example when the third harmonic lies on a lower side relative to the other first and second harmonics, information on a larger profile in the image is removed together with the third harmonic simultaneously, causing highly degraded visibility. On the other hand, when the third harmonic on a higher frequency side is removed, information on a fine shape or an edge is removed together with the third harmonic simultaneously. In addition, the third harmonic is frequency component with small spectrum intensity as illustrated in FIG. 13. Consequently, it has been proved that the third harmonic is distinguishable in a flat region with a little variation in pixel value (intensity variation), and is not recognized in a region out of the flat region.

The present invention based on the above finding adopts the following configuration. One embodiment of the present invention discloses an X-ray diagnostic apparatus having an X-ray emitter configured to emit X-rays to a subject; an X-ray detector configured to detect X-rays transmitting through the subject; and a grid disposed on an X-ray incidence side of the X-ray detector to remove scattered X-rays, and is configured to obtain an image in accordance with output from the X-ray detector. The X-ray diagnostic apparatus includes a peak frequency detector configured to detect a peak frequency of a first harmonic in a moiré pattern of the grid appearing in the image; a first and second harmonic remover configured to remove the first harmonic and a second harmonic in the moiré pattern from the image in accordance with the peak frequency of the first harmonic to obtain a first and second harmonic removed image; a third harmonic extracting-filter generating unit configured to calculate a peak frequency of a third harmonic in the moiré pattern in accordance with the peak frequency of the first harmonic to generate a third harmonic extracting filter to extract the third harmonic; a third harmonic extracting unit configured to extract the third harmonic from the first and second harmonic removed image based on the third harmonic extracting filter; a third harmonic subtracting unit configured to subtract the extracted third harmonic from the first and second harmonic removed image to obtain a third harmonic removed image; a flatness calculating unit configured to calculate flatness in the first and second harmonic removed image to obtain flatness information; and an output selecting unit configured to output the third harmonic removed image within a flat region of the flatness information, and output the first and second harmonic removed image within a region out of the flat region of the flatness information.

According to the X-ray diagnostic apparatus in one embodiment of the present invention, the third harmonic extracting-filter generating unit calculates the peak frequency of the third harmonic in the moiré pattern in accordance with the peak frequency of the first harmonic to generate the third harmonic extracting filter to extract the third harmonic. The third harmonic extracting unit extracts the third harmonic from the first and second harmonic removed image based on the third harmonic extracting filter. The third harmonic subtracting unit subtracts the extracted third harmonic from the first and second harmonic removed image to obtain the third harmonic removed image. Consequently, the third harmonic in the moiré pattern remaining in the moiré-pattern removed image enables to be removed.

Moreover, the third harmonic in the moiré pattern is a frequency component with smaller spectrum intensity. Accordingly, the third harmonic is distinguishable in the flat region of the image with a little intensity variation and is not recognized in the region out of the flat region. Consequently, the output selecting unit outputs the third harmonic removed image in the flat region of the flatness information acquired through calculating flatness by the flatness calculating unit, and outputs the first and second harmonic removed image in the region out of the flat region of the flatness information. That is, the third harmonic removed image is outputted in the flat region where the third harmonic of the moiré pattern is distinguishable in the first and second harmonic removed image. Accordingly, degradation in visibility of the image enables to be suppressed, and the third harmonic in the moiré pattern remaining in the moiré-pattern removed image enables to be removed.

Moreover, in the X-ray diagnostic apparatus in the embodiment of the present invention, it is preferable that the flatness calculating unit includes an amount of intensity-variation calculating unit configured to calculate an amount of intensity variation between a target pixel to be processed and pixels therearound to obtain flatness information. Consequently, the amount of intensity-variation calculating unit enables to obtain flatness information representing flatness in the first and second harmonic removed image by calculating the amount of intensity variation between the target pixel and the pixels therearound.

Moreover, in the X-ray diagnostic apparatus in the embodiment of the present invention, the amount of intensity-variation calculating unit preferably subtracts an arithmetic mean of the target pixel and the pixels therearound from a pixel value of the target pixel to obtain flatness information. Consequently, the amount of intensity-variation calculating unit enables to obtain flatness information by subtracting the arithmetic mean of the target pixel and the pixels therearound from the pixel value of the target pixel to calculate the amount of intensity variation.

Moreover, in the X-ray diagnostic apparatus in the embodiment of the present invention, the flatness calculating unit preferably includes a normalizing unit configured to divide an amount of intensity variation of each pixel in the flatness information by a corresponding pixel value in the first and second harmonic removed image to perform normalization. That is, a pixel with a higher pixel value is likely to have a larger amount of intensity variation, whereas a pixel with a lower pixel value is likely to have a smaller amount of intensity variation. The pixel of higher intensity and that with the pixel of lower intensity have the same amount of intensity variation, but differ from each other in weight. Accordingly, dividing the amount of intensity variation of each pixel by the corresponding pixel value achieves comparison of the amount of intensity variation between the pixels of high and lower intensity on the same basis.

Moreover, in the X-ray diagnostic apparatus in the embodiment of the present invention, the flatness calculating unit preferably includes a smoothing unit configured to average an amount of intensity variation for every region into which the flatness information is divided by a plurality of pixels and to perform smoothing by applying the arithmetic mean to each pixel of the divided region. Smoothing the amount of intensity variation allows the output selecting unit to perform selection and output in any region. In addition, regions each regarded as the flat region and scattered out of the flat region enable to be processed as regions out of the flat region. Outputting the third harmonic removed image to the flat regions scattered out of the flat region may lead to visibility degradation.

Moreover, the X-ray diagnostic apparatus in the embodiment of the present invention preferably includes a low-pass filtering unit configured to perform one-dimensional low-pass filtering to an image of the third harmonic extracted by the third harmonic extracting unit along fringes of the third harmonic. An oblique pattern relative to the fringes of the third harmonic extracted in addition to the third harmonic in the moiré pattern enables to be removed.

Moreover, another embodiment of the present invention discloses a storage medium storing an X-ray diagnostic program to execute processing by a computer to an image taken via a grid configured to remove scattered X-rays. The program includes detecting a peak frequency of a first harmonic in a moiré pattern of the grid appearing in the image; removing the first harmonic and a second harmonic in the moiré pattern from the image in accordance with the peak frequency of the first harmonic to obtain a first and second harmonic removed image; calculating a peak frequency of a third harmonic in the moiré pattern in accordance with the peak frequency of the first harmonic to generate a third harmonic extracting filter to extract the third harmonic; extracting the third harmonic from the first and second harmonic removed image based on the third harmonic extracting filter; subtracting the third harmonic from the first and second harmonic removed image to obtain a third harmonic removed image; calculating flatness in the first and second harmonic removed image to obtain flatness information; and outputting the third harmonic removed image within a flat region of the flatness information, and outputting the first and second harmonic removed image within a region out of the flat region of the flatness information.

According to the storage medium storing the X-ray diagnostic program in the embodiment of the present invention, the peak frequency of the third harmonic in the moiré pattern is calculated in accordance with the peak frequency of the first harmonic in the moiré pattern, whereby the third harmonic extracting filter to extract the third harmonic is generated. Subsequently, the third harmonic is extracted from the first and second harmonic removed image based on the third harmonic extracting filter. Thereafter, the extracted third harmonic is subtracted from the first and second harmonic removed image to obtain the third harmonic removed image. Consequently, the third harmonic in the moiré pattern remaining in the moiré-pattern removed image enables to be removed.

Moreover, since the third harmonic in the moiré pattern is a frequency component with smaller spectrum intensity. Accordingly, the third harmonic is distinguishable in the flat region of the image with a little intensity variation and is not recognized in the region out of the flat region. Consequently, flatness in the first and second harmonic removed image is calculated to obtain flatness information. The third harmonic removed image is outputted in the flat region of the flatness information, and the first and second harmonic removed image is outputted in the region out of the flat region of the flatness information. That is, the third harmonic removed image is outputted in the flat region where the third harmonic of the moiré pattern is distinguishable in the first and second harmonic removed image. Accordingly, degradation in visibility of the image enables to be suppressed, and the third harmonic in the moiré pattern remaining in the moiré-pattern removed image enables to be removed.

Advantageous Effects of Invention

According to the X-ray diagnostic apparatus and the storage medium storing the X-ray diagnostic program of the present invention, the peak frequency of the third harmonic in the moiré pattern is calculated in accordance with the peak frequency of the first harmonic in the moiré pattern, whereby the third harmonic extracting filter to extract the third harmonic is generated. Subsequently, the third harmonic is extracted from the first and second harmonic removed image based on the third harmonic extracting filter. Thereafter, the extracted third harmonic is subtracted from the first and second harmonic removed image to obtain the third harmonic removed image. Consequently, the third harmonic in the moiré pattern remaining in the moiré-pattern removed image enables to be removed.

Moreover, since the third harmonic in the moiré pattern is a frequency component with smaller spectrum intensity. Accordingly, the third harmonic is distinguishable in the flat region of the image with a little intensity variation and is not recognized in the region out of the flat region. Consequently, flatness in the first and second harmonic removed image is calculated to obtain flatness information. The third harmonic removed image is outputted in the flat region of the flatness information, and the first and second harmonic removed image is outputted in the region out of the flat region of the flatness information. That is, the third harmonic removed image is outputted in the flat region where the third harmonic of the moiré pattern is distinguishable in the first and second harmonic removed image. Accordingly, degradation in visibility of the image enables to be suppressed, and the third harmonic in the moiré pattern remaining in the moiré-pattern removed image enables to be removed.

BRIEF DESCRIPTION OF DRAWINGS

FIG. 5 illustrates one example of a low-pass filter: 5(a) illustrating an explanatory view of a vertical low-pass filter (LPF) processing, and 5(b) illustrating one example of a vertical low-pass filter (LPF).

REFERENCE SIGNS LIST

Figure 1:
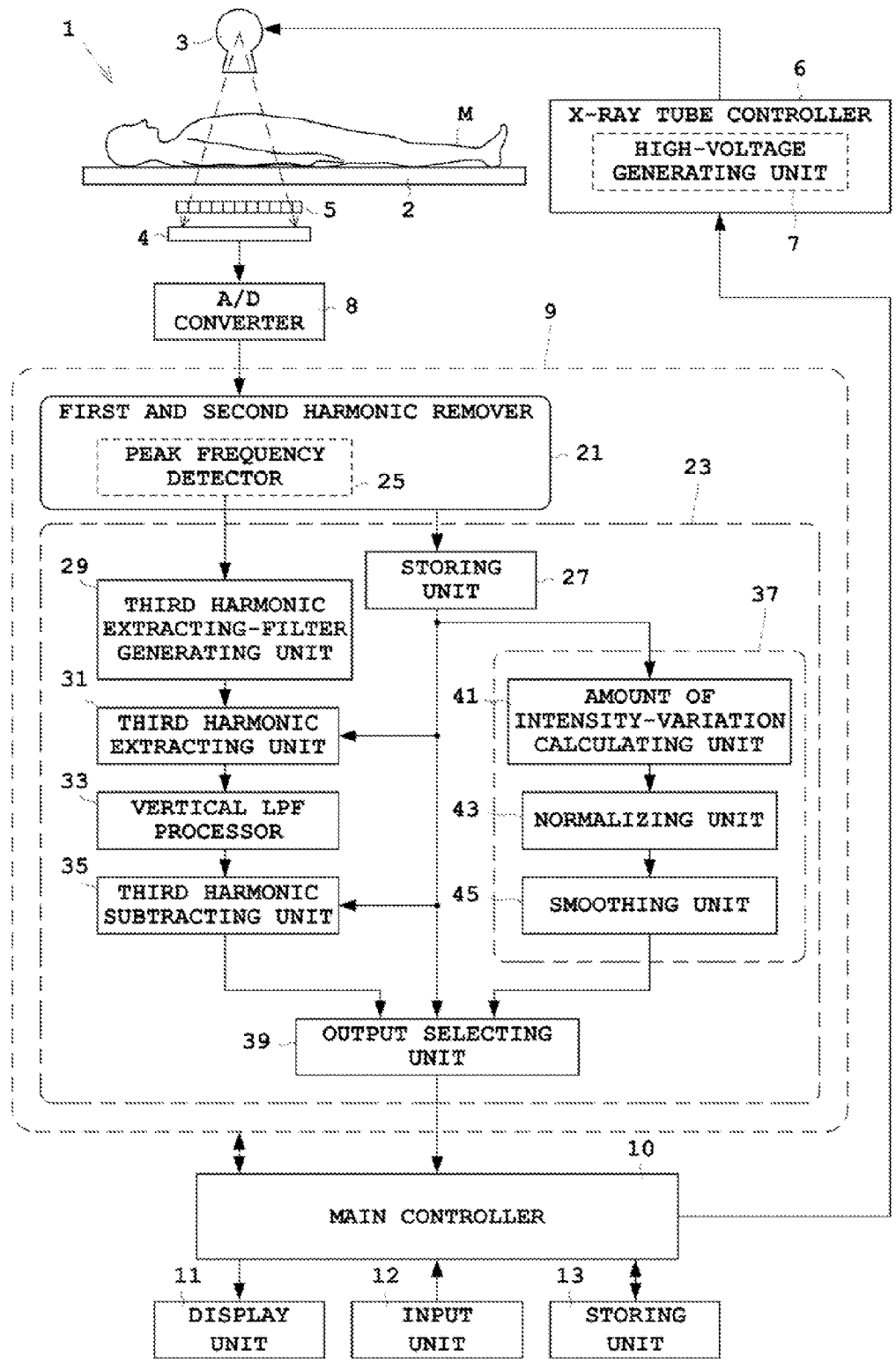
FIG. 1 is a block diagram schematically illustrating an X-ray diagnostic apparatus according to one embodiment of the present invention.

1 . . . X-ray diagnostic apparatus
3 . . . X-ray tube
4 . . . X-ray detector
5 . . . scattered-radiation removal grid
9 . . . image processor
10 . . . main controller
21 . . . first and second harmonic remover
23 . . . third harmonic remover
25 . . . peak frequency detector
29 . . . third harmonic extracting-filter generating unit
31 . . . third harmonic extracting unit
33 . . . vertical low-pass filtering unit (vertical LPF processor)
35 . . . third harmonic subtracting unit
37 . . . flatness calculating unit
39 . . . output selecting unit
41 . . . amount of intensity-variation calculating unit
43 . . . normalizing unit
45 . . . smoothing unit

DESCRIPTION OF EMBODIMENTS

Figure 2:
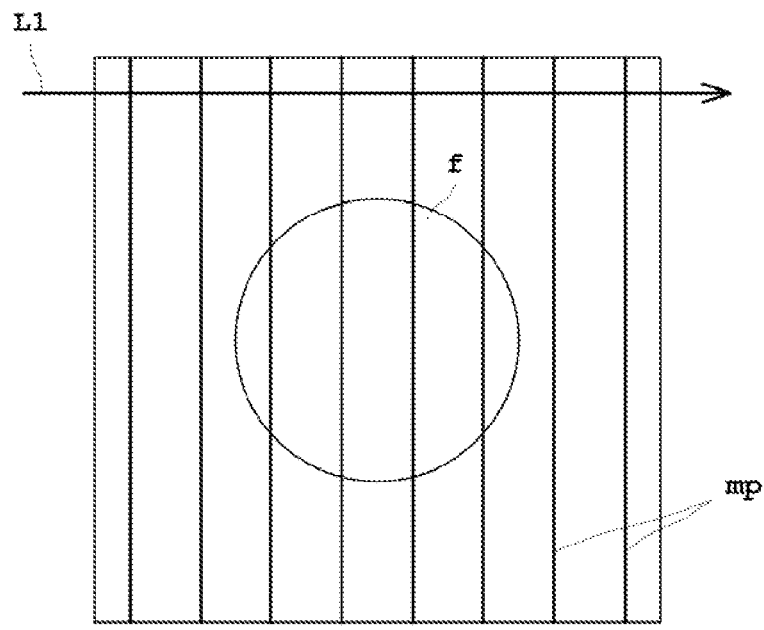
FIG. 2 is an explanatory view of a moiré pattern.
Figure 3:
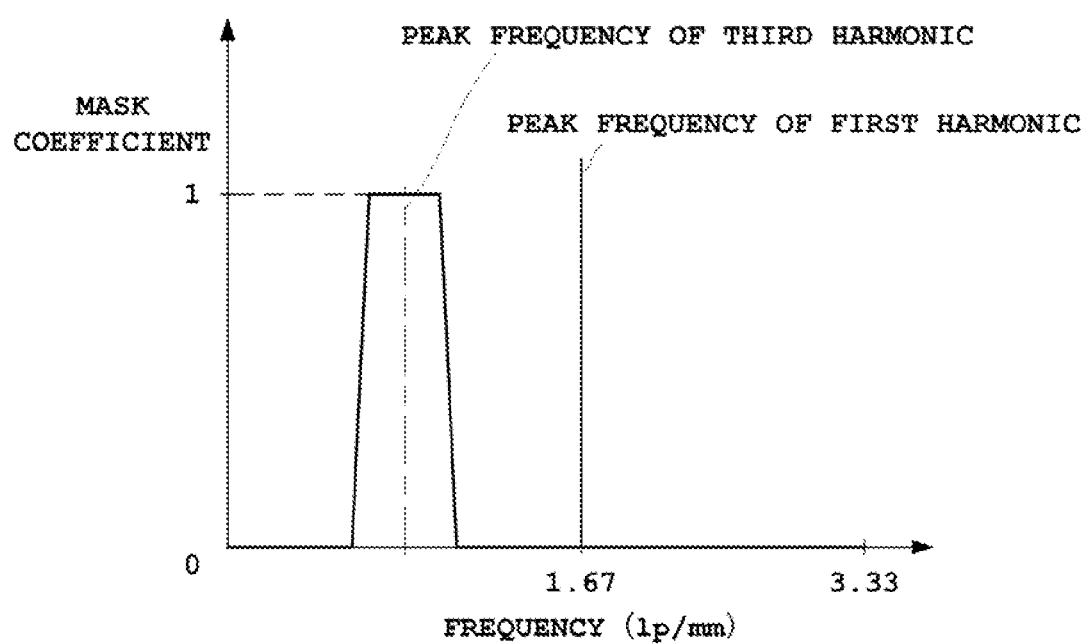
FIG. 3 is an explanatory view of generating an extracting filter for a third harmonic in the moiré pattern.
Figure 4:
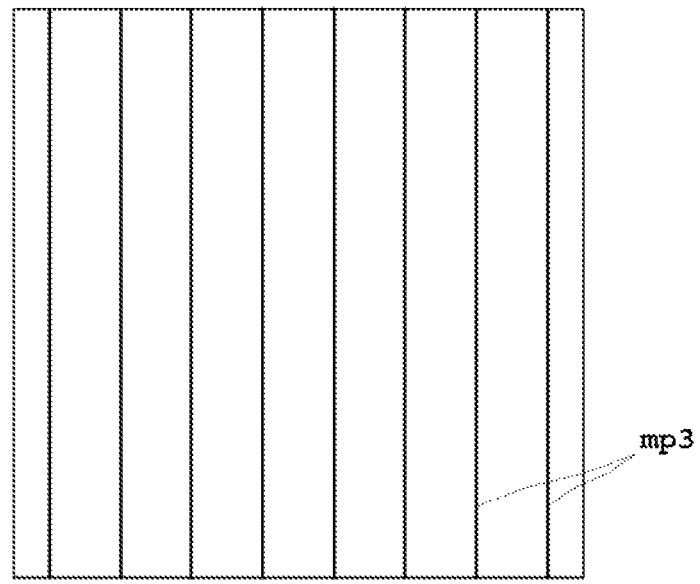
FIG. 4 illustrates one example of the third harmonic in the moiré pattern.
Figure 6:
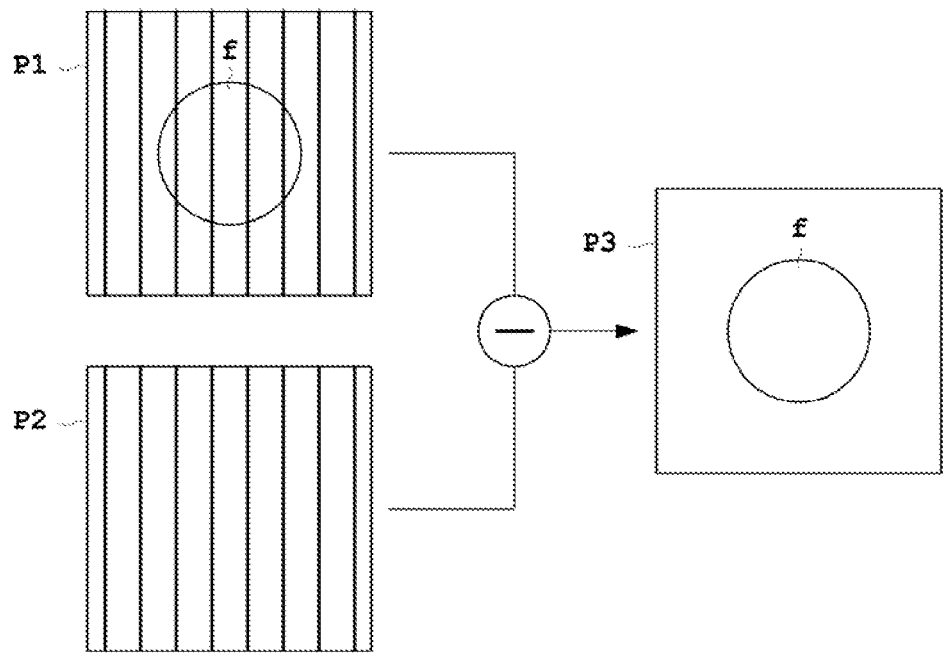
FIG. 6 is an explanatory view of removing the third harmonic in the moiré pattern.
Figure 7:
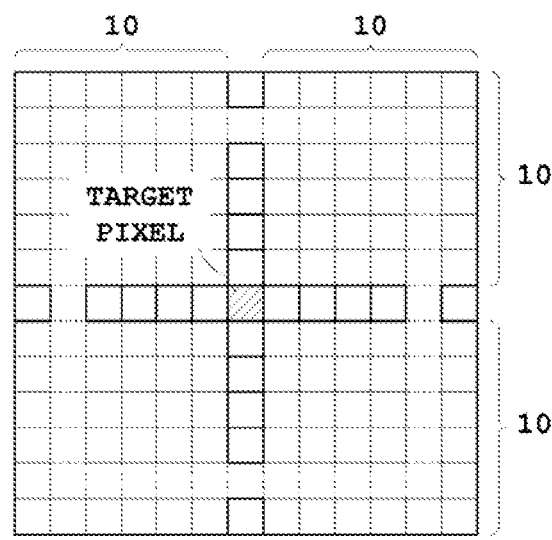
FIG. 7 is an explanatory view of calculating an amount of intensity variation.
Figure 8:
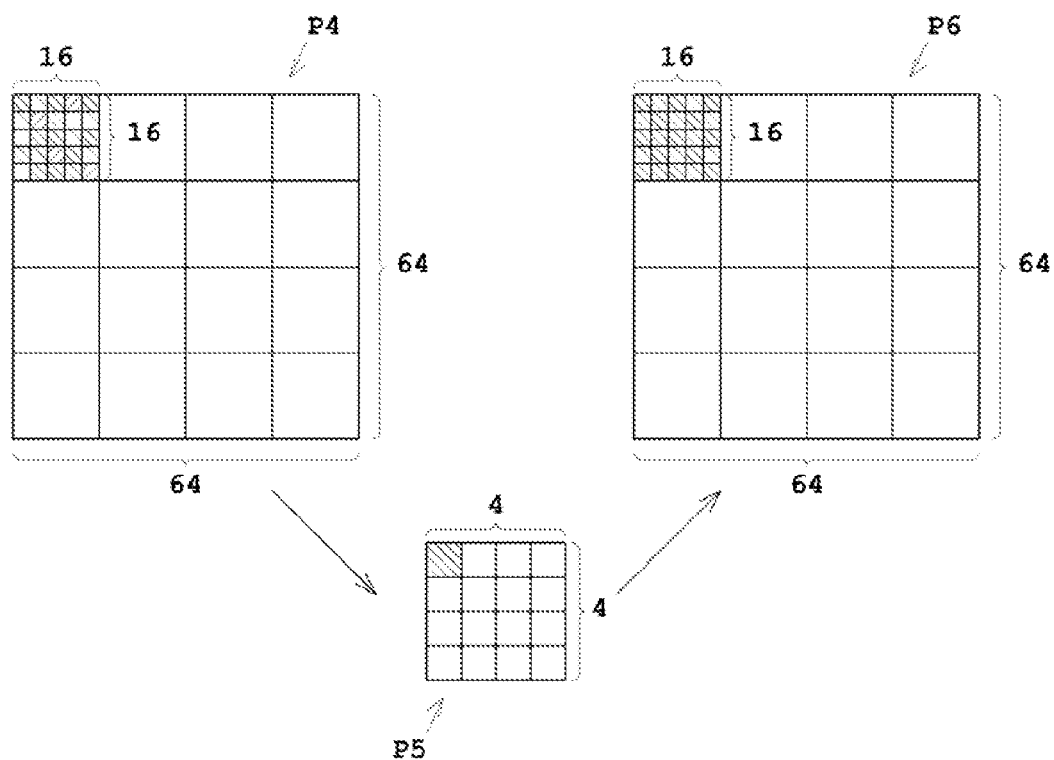
FIG. 8 is an explanatory view of smoothing.
Figure 9:
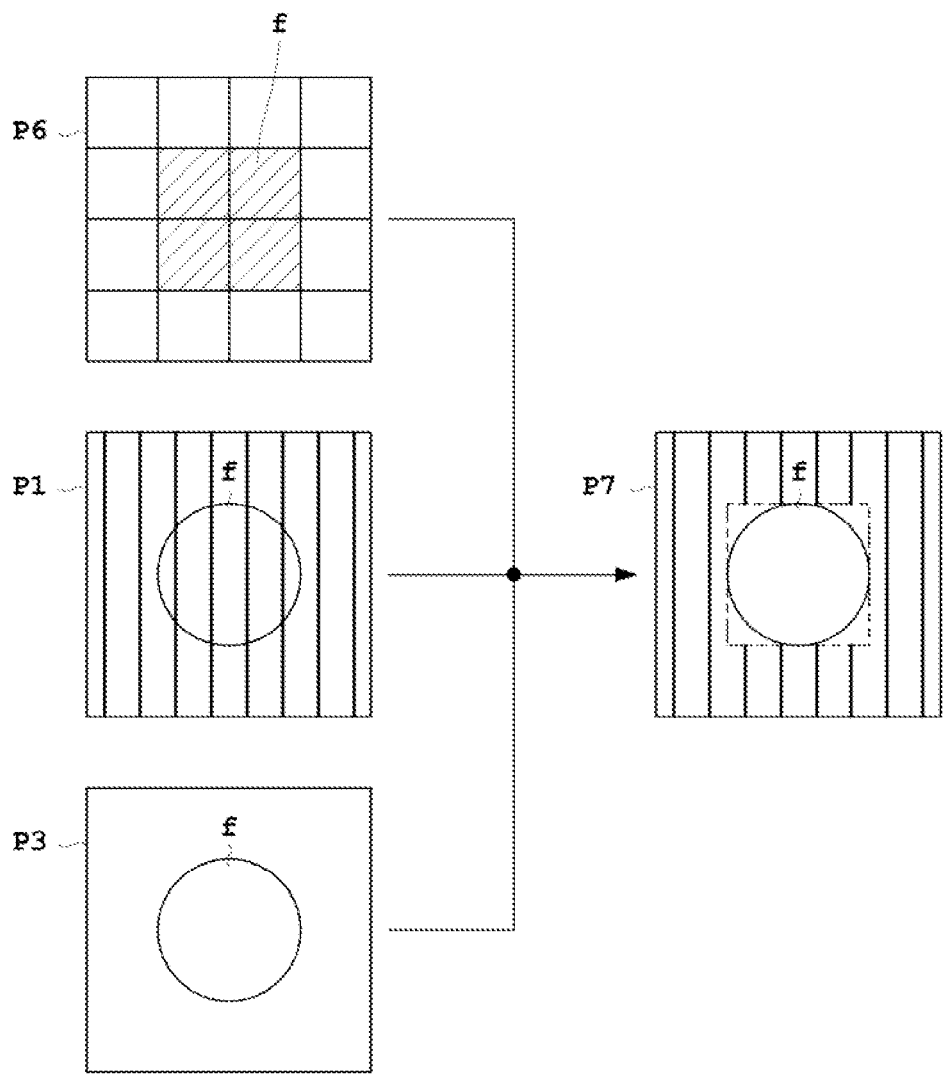
FIG. 9 is an explanatory view of selection and output.

Description will be given hereinafter of embodiments of the present invention with reference to drawings. FIG. 1 is a block diagram schematically illustrating an X-ray diagnostic apparatus according to one embodiment of the present invention. FIG. 2 is an explanatory view of a moiré pattern. FIG. 3 is an explanatory view of generating an extracting filter for a third harmonic in the moiré pattern. FIG. 4 illustrates one example of the third harmonic in the moiré pattern. FIG. 5(a) illustrates an explanatory view of a vertical low-pass filter (LPF) processing, and 5(b) illustrates one example of a vertical low-pass filter (LPF). FIG. 6 is an explanatory view of removing the third harmonic in the moiré pattern. FIG. 7 is an explanatory view of calculating an amount of intensity variation. FIG. 8 is an explanatory view of a smoothing processing. FIG. 9 is an explanatory view of selection and output.

Reference is now made to FIG. 1. An X-ray diagnostic apparatus 1 includes a top board 2 configured to support a subject M placed thereon; an X-ray tube 3 configured to emit X-rays to the subject M; an X-ray detector 4 opposed to the X-ray tube 3 across the subject M and configured to detect X-rays transmitting through the subject M; and a grid 5 disposed on a side of the X-ray detector 4 where X-rays enter and configured to remove scattered X-rays. Here, the X-ray tube 3 corresponds to an X-ray emitter in the present invention.

An X-ray tube controller 6 performs control to the X-ray tube 3 necessary for X-ray emission. The X-ray tube controller 6 includes a high-voltage generating unit 7 that generates tube voltage or tube current of the X-ray tube 3. The X-ray tube controller 6 emits X-rays from the X-ray tube 3 in accordance with conditions of X-rays, such as tube voltage, tube current, or irradiation time, set by an input unit 12 mentioned later.

The X-ray detector 4 detects X-rays emitted from the X-ray tube 3, and outputs X-ray detection signals corresponding to intensity distribution of the X-rays. The X-ray detector 4 is composed of a flat panel X-ray detector (FPD), an image intensifier, or the like. For instance, the X-ray detector 4 has a pixel pitch of 0.15 μm and resolution of 3.33 lp/mm. For instance, the grid 5 has grid density of 50 line/cm (5 lp/mm).

An A/D converter 8 and an image processor 9 are provided in this order on the downstream of the X-ray detector 4. The A/D converter 8 converts analog X-ray detection signals outputted from the X-ray detector 4 into digital signals. The image processor 9 performs various processes to an image in accordance with the digital X-ray detection signals outputted from the X-ray detector 4. In addition, the X-ray diagnostic apparatus 1 further includes a main controller 10 configured to control en bloc each element of the apparatus 1, a display unit 11 configured to display an image processed by the image processor 9, an input unit 12 configured to perform input setting or various operations by an operator, and a storing unit 13 configured to store the processed image.

The main controller 10 is formed by a central processing unit (CPU) or the like, and executes various programs. For instance, the main controller 10 controls the top board 2 with the subject M placed thereon, the X-ray tube 3, or the X-ray detector 4 so as to move in a given position. The display unit 11 is formed by a monitor or the like. The input unit 12 is formed by a keyboard, a mouse, and the like. The storing unit 13 is formed by a storage medium such as a ROM (Read-only Memory), a RAM (Random-Access Memory), or a hard disk.

The image processor 9 includes a first and second harmonic remover 21 and a third harmonic remover 23 that remove a moiré pattern of the grid 5 appearing in the image obtained in accordance with output from the X-ray detector 4. The first and second harmonic remover 21 includes a peak frequency detector 25 that detects a peak frequency of a first harmonic in the moiré pattern of the grid 5 appearing in the image. The first and second harmonic remover 21 removes the first harmonic and the second harmonic in the moiré pattern from the image in accordance with the peak frequency of the first harmonic to obtain a first and second harmonic removed image.

Figure 13:
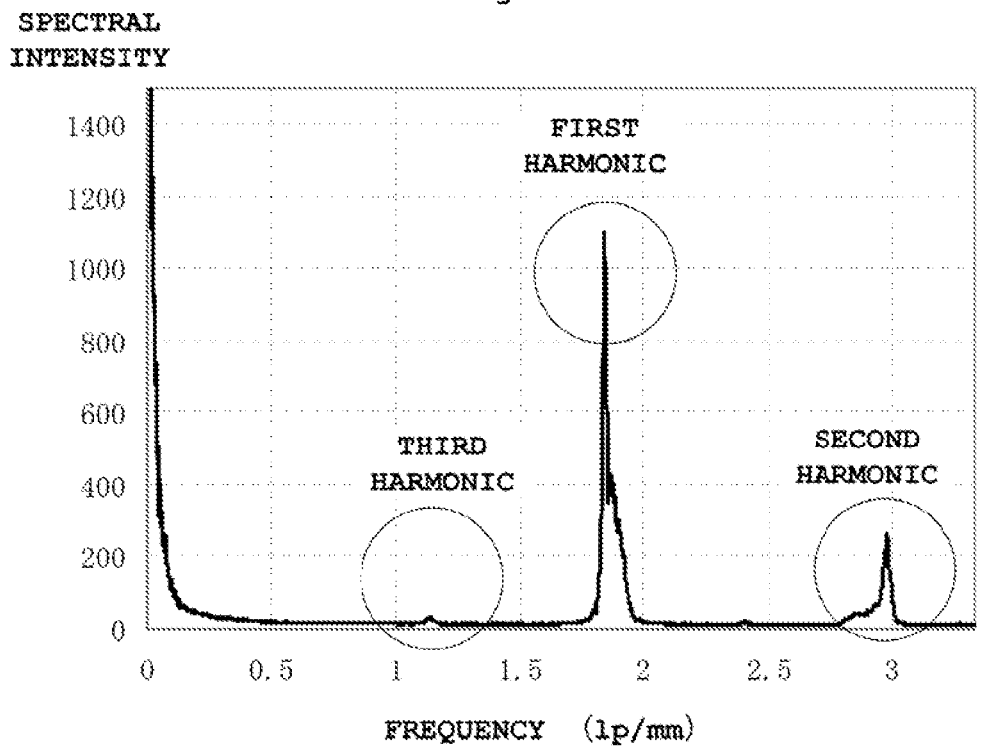
FIG. 13 illustrates one example of a result of one-dimensional Fourier transform to the image.

The first and second harmonic remover 21 removes the first and second harmonics in the moiré pattern of the grid 5 appearing in the image. As illustrated in FIG. 2, the first and second harmonic remover 21 firstly performs one-dimensional Fourier transform to the image having the moiré pattern (numeral mp) appearing therein along a lateral (orthogonal relative to fringes of the moiré pattern) pixel line (numeral L1). For instance, the one-dimensional Fourier transform is performed in order from the pixel line on the upper end of the image. The peak frequency detector 25 detects a peak frequency representing the first harmonic in the moiré pattern from results of the Fourier transform (FIG. 13). The peak frequency detector 25 detects a set given peak frequency from a plurality of peak frequencies detected in order from the upper end of the image. The second harmonic enables to be calculated from the peak frequency of the first harmonic since the second harmonic is twice (integral multiple) the first harmonic. A filter used for extracting the first and second harmonics in the moiré pattern is generated in accordance with the peak frequencies of the acquired first and second harmonics. The first and second harmonics are extracted using the filter. Thereafter, the extracted first and second harmonics are subtracted from the image with the moiré pattern appearing therein. Consequently, the first and second harmonic removed image is obtained with the first and second harmonics in the moiré pattern being removed therefrom. Here in FIG. 2, a flat region of the subject M in the image is denoted by the numeral f.

As illustrated in FIG. 1, the third harmonic remover 23 includes a storing unit 27, a third harmonic extracting filter generating unit 29, a third harmonic extracting unit 31, a vertical low-pass filtering unit (vertical LPF processor) 33, a third harmonic subtracting unit 35, a flatness calculating unit 37, and an output selecting unit 39. The first and second harmonic removed image from which the first and second harmonics in the moiré pattern are removed by the first and second harmonic remover 21 is stored in the storing unit 27.

Figure 14:
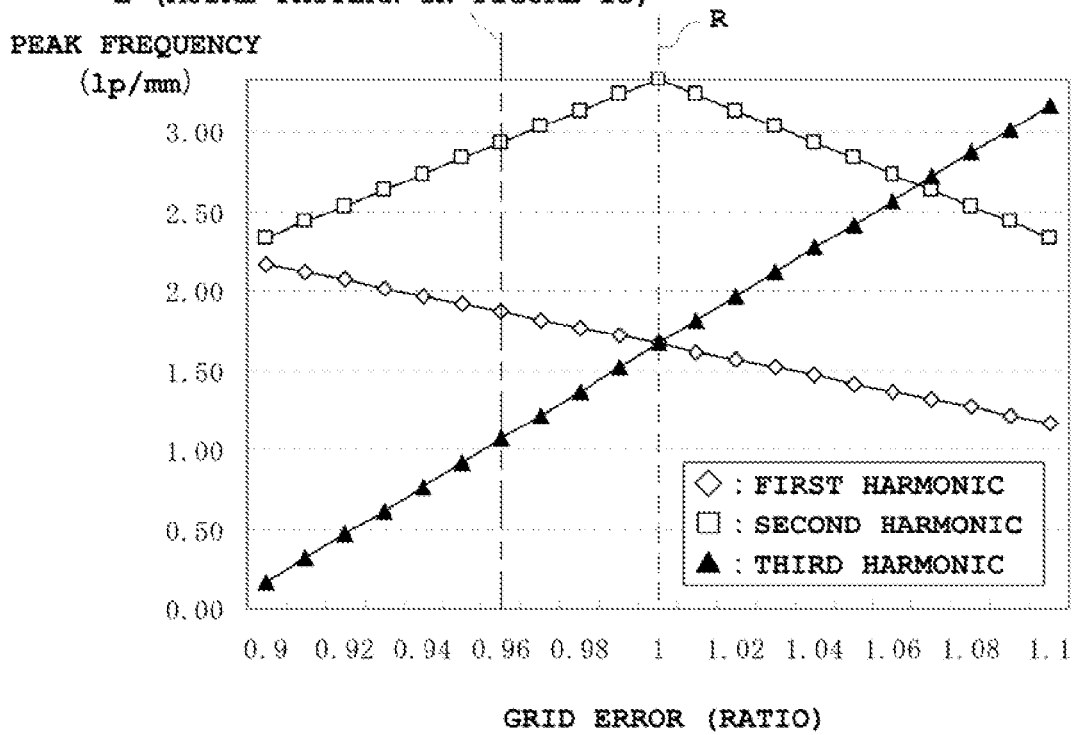
FIG. 14 illustrates a relationship between a grid error and the peak frequencies of the harmonics in the moiré pattern.

The third harmonic extracting-filter generating unit 29 calculates a peak frequency of the third harmonic in the moiré pattern in accordance with the peak frequency of the first harmonic to generate a third harmonic extracting filter used for extracting the third harmonic. The peak frequency of the first harmonic detected by the peak frequency detector 25 is applied to the peak frequency of the first harmonic. The third harmonic in the moiré pattern is three-times the first harmonic in the moiré pattern. When the third harmonic is larger than the Nyquist frequency Ny of 3.33 lp/mm, the peak frequency of the third harmonic lies in a position where the third harmonic is folded at 3.33 lp/mm. That is, when the peak frequency of the first harmonic is 1.72 lp/mm, the peak frequency of the third harmonic is 1.72×3=5.16 lp/mm. At this time, since the third harmonic is larger than the Nyquist frequency Ny of 3.33 lp/mm, the third harmonic is folded at a position of 3.33 lp/mm. Then, the peak frequency of the third harmonic is 3.33−(5.16−3.33)=1.50 lp/mm. When the peak frequency of the first harmonic is 1.72 lp/mm, the grid error (ratio) is 0.99 in FIG. 14. As illustrated in FIG. 3, the third harmonic extracting filter is generated with the calculated peak frequency of the third harmonic having a given band.

The third harmonic extracting unit 31 extracts the third harmonic from the first and second harmonic removed image based on the third harmonic extracting filter. The first and second harmonic removed image is given from the storing unit 27. For instance, the third harmonic is extracted by filtering the lateral pixel lines in the first and second harmonic removed image using the third harmonic extracting filter. Such extraction is performed for example for every line in order from the upper end of the first and second harmonic removed image. This achieves extraction of an image of the third harmonic in the moiré pattern as illustrated in FIG. 4.

The extracted image of the third harmonic, however, contains an oblique pattern denoted by numeral n in FIG. 5(a) in addition to the third harmonic in the moiré pattern. This occurs because a pattern in the first and second harmonic removed image having the same frequency as the third harmonic extracting filter is extracted. In other words, the third harmonic in the moiré pattern having a period d1 is extracted on a lateral pixel line L2, and a pattern having the same period (d2=d1) in the first and second harmonic removed image is also extracted.

Then, the vertical LPF processor 33 performs one-dimensional low-pass filter (LPF) processing vertically along the fringes of the third harmonic extracted by the third harmonic extracting unit 31. FIG. 5(a) illustrates the fringes of the third harmonic in the moiré pattern denoted by numeral mp3. That is, the LPF processing is performed vertically along the fringes of the third harmonic. The vertical LPF processing performs filtering to each pixel in the extracted image of the third harmonic using the filter illustrated in FIG. 5(b). The filter illustrated in FIG. 5(b) is a vertical pixel line. For instance, a pixel line is used having seventeen pixels including a target pixel to be processed and upper eight pixels and lower eight pixels across the target pixel. The average of the pixel values of the seventeen pixels prior to be processed is calculated, and the calculated arithmetic mean is given as a new pixel value of the target pixel. Such process is performed to each pixel, whereby the vertical pixels of the image are smoothed to remove the oblique pattern denoted by the numeral n in FIG. 5(a). Then, the image of the third harmonic in the moiré pattern as illustrated in FIG. 4 is obtained. The vertical LPF processor 33 corresponds to a low-pass filtering unit in the present invention. In FIG. 5(a), the fringes of the third harmonic in the moiré pattern are arranged laterally. On the other hand, when the fringes are arranged vertically, a one-dimensional low-pass filter (LPF) processing is performed laterally along the fringes.

The third harmonic subtracting unit 35 subtracts the extracted third harmonic from the first and second harmonic removed image to obtain the third harmonic removed image. That is, the third harmonic subtracting unit 35 subtracts an extracted image P2 of the third harmonic from the first and second harmonic removed image P1 as illustrated in FIG. 6. Consequently, a third harmonic removed image P3 is obtained.

As illustrated in FIG. 1, the flatness calculating unit 37 calculates flatness in the first and second harmonic removed image to acquire flatness information. The flatness calculating unit 37 calculates the flatness information in parallel with obtaining the third harmonic removed image in which the third harmonic is extracted and removed. The flatness information is used for distinguishing a flat region and a non-flat region of a structure (a region out of the flat region) of the first and second harmonic removed image. For instance, in radiography to legs of the subject M, examples of the flat region include flesh and examples of the region out of the flat region include a bone. The flatness calculating unit 37 includes an amount of intensity-variation calculating unit 41, a normalizing unit 43, and a smoothing unit 45.

The amount of intensity-variation calculating unit 41 calculates an amount of intensity variation of the target pixel to be processed and the pixels therearound to acquire the flatness information. Specifically, the amount of intensity-variation calculating unit 41 subtracts the arithmetic mean of the target pixel and the pixels therearound from the pixel value of the target pixel to acquire the flatness information. That is, the amount of intensity-variation calculating unit 41 averages 21×21 pixels, i.e., the target pixel and ten pixels from side to side and up and down from the target pixel, for example, to obtain an arithmetic mean, and subtracts the arithmetic mean from the pixel value of the target pixel. That is, for example, when the arithmetic mean of the pixel values of 21×21 pixels is denoted by A and the pixel value of the target pixel is denoted by B, an amount of intensity variation C1 is given: $C1=|B-A|$. Such processing is performed to each pixel in the first and second harmonic removed image. A new image expressed by the amount of intensity variation C1 in this way is obtained as the flatness information.

The normalizing unit 43 performs normalization by dividing the amount of intensity variation of each pixel in the flatness information by a corresponding pixel value in the first and second harmonic removed image. That is, an amount of intensity variation C2 after normalization is expressed by $C2=|B-A|/B$. The pixel with a higher pixel value is likely to have a larger amount of intensity variation (variation in pixel value), whereas the pixel with a lower pixel value is likely to have a smaller amount of intensity variation. For instance, it is assumed that there exist a target pixel with a pixel value of 1000 and a target pixel with a pixel value of 10. When both have an amount of intensity variation of 2, both have the same amount of intensity variation. On the other hand, a weight with the pixel value of 1000 and the amount of intensity variation of 2 is 2/1000=0.002, whereas a weight with the pixel value of 10 and the amount of intensity variation of 2 is 2/10=0.2, and thus both differ from each other. Consequently, comparison enables to be made on the same basis between the amount of intensity variation of the higher intensity pixel and that of the lower intensity pixel.

The smoothing unit 45 performs smoothing by averaging the amount of intensity variation for every region into which the flatness information is divided by a plurality of pixels and applying the arithmetic mean to each pixel of the divided region. For instance, when flatness information P4 is defined by 64×64 pixels as illustrated in FIG. 8, the smoothing unit 45 performs average by 16×16 pixels, for example, to reduce the flatness information into one pixel. Accordingly, reduced flatness information P5 of 4×4 pixels is obtained. Thereafter, the flatness information P5 of 4×4 pixels is returned (enlarged) into original 64×64 pixels to obtain smoothed flatness information P6. When the flatness information P5 of one pixel is returned to the flatness information P6 of 16×16 pixels, the amount of intensity variation of one pixel in the flatness information P5 is given to every amount of intensity variation of 16×16 pixels in the flatness information P6.

The output selecting unit 39 outputs the third harmonic removed image in the flat region of the flatness information, and outputs the first and second harmonic removed image in the region out of the flat region of the flatness information. That is, as illustrated in FIG. 9, the output selecting unit 39 selects output of either the first and second harmonic removed image P1 or the third harmonic removed image P3 in accordance with the flatness information P6. When the normalized and smoothed amount of intensity variation in the flatness information P6 is the threshold or more, the image is identified as a flat region. When the normalized and smoothed amount of intensity variation in the flatness information P6 is less than the threshold, the image is identified as a region out of the flat region. Since each of the pixels (16×16 pixels) of the divided region averaged by 16×16 pixels by the smoothing unit 45 has the same amount of intensity variation, the output selecting unit 39 selects output in region of 16×16 pixels. As illustrated in FIG. 9, the third harmonic removed image P3 is outputted in the flat region (numeral f) of the flatness information P6. On the other hand, the first and second harmonic removed image P1 is outputted in the region out of the flat region of the flatness information P6.

Figure 10:
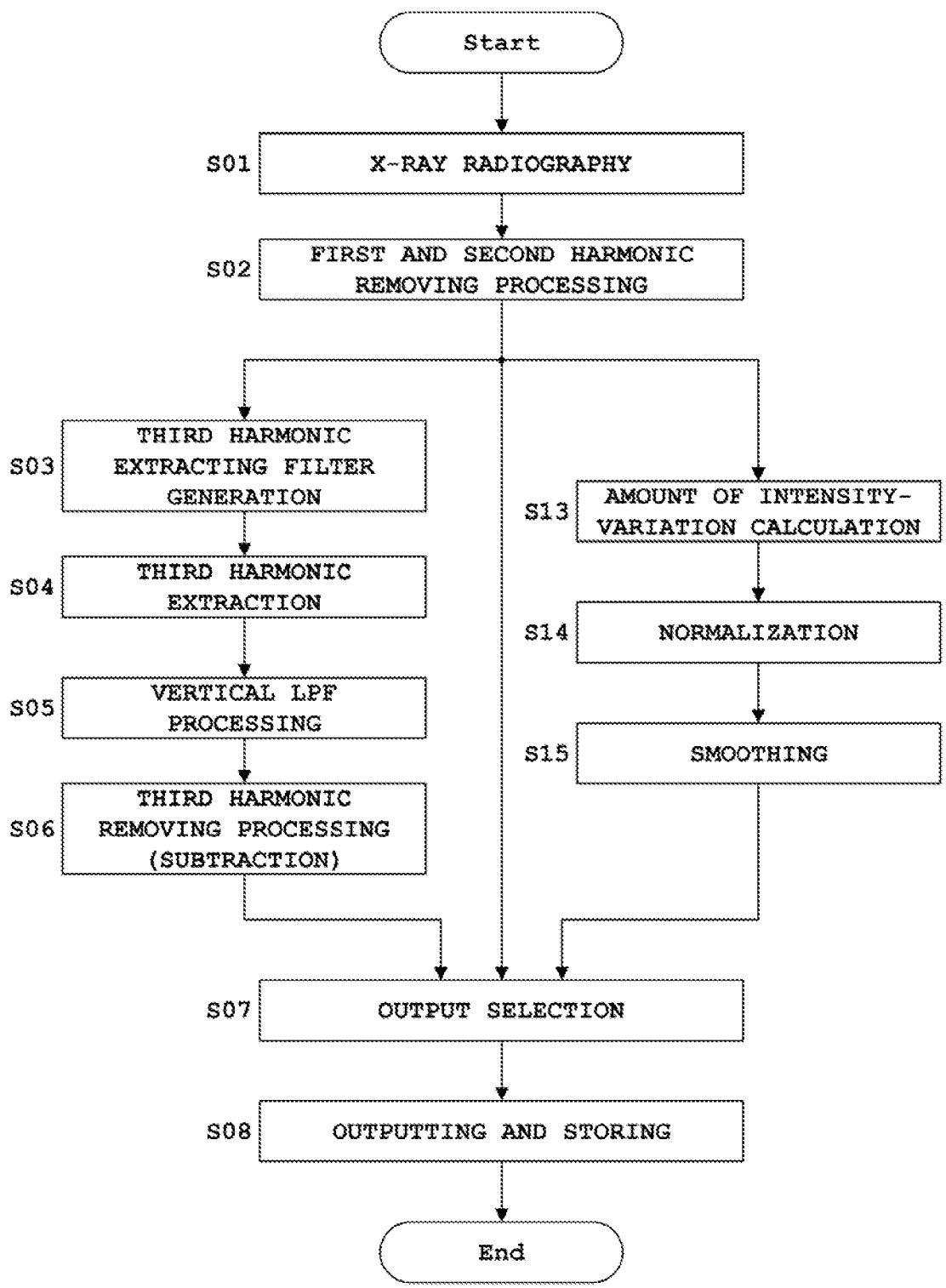
FIG. 10 is a flow chart illustrating operation of the X-ray diagnostic apparatus according to the embodiment of the present invention.
Figure 11:
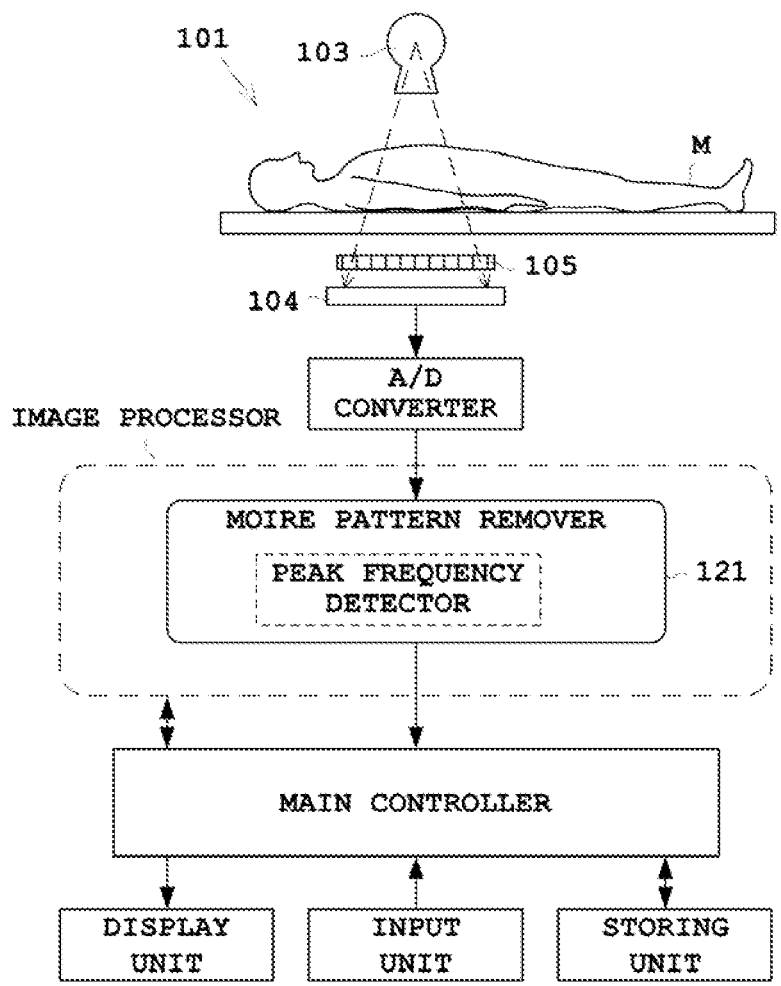
FIG. 11 is a block diagram schematically illustrating a conventional X-ray diagnostic apparatus.
Figure 12:
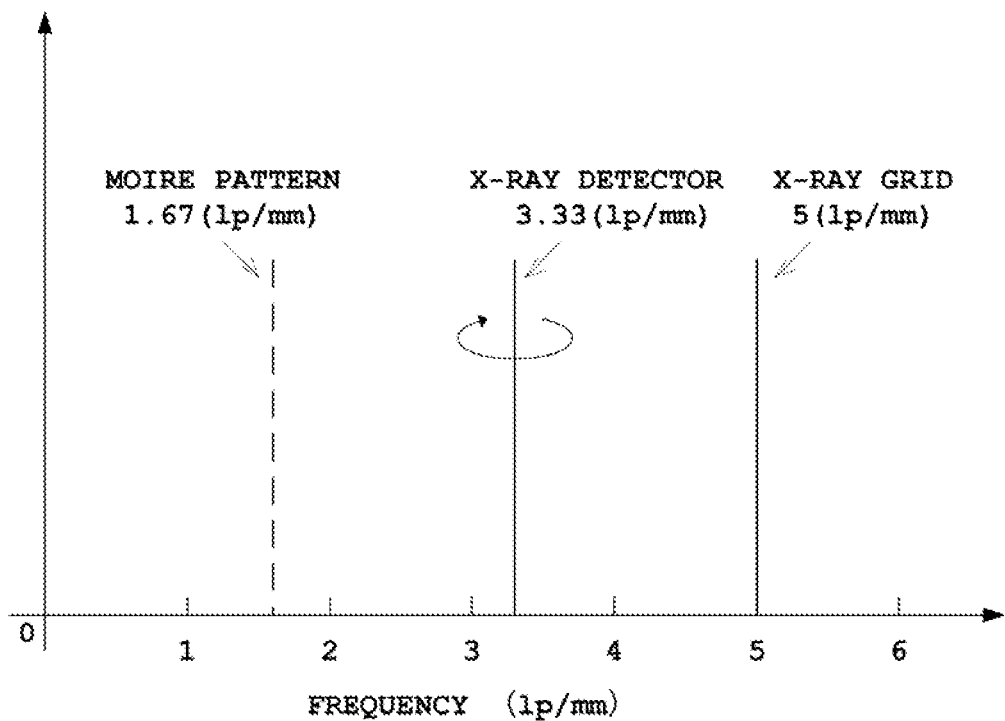
FIG. 12 is an explanatory view of a frequency of the moiré pattern with the X-ray detector and the grid.

Next, description will be given operation of the X-ray diagnostic apparatus 1 with reference to FIG. 10 along with a flow chart.

Step S01 X-Ray Radiography

As illustrated in FIG. 1, the X-ray diagnostic apparatus 1 emits X-rays from the X-ray tube 3 in accordance with X-ray conditions such as tube voltage, tube current, and irradiation time, that are set by the X-ray tube controller 6. The X-rays from the X-ray tube 3 transmit through the subject M to enter into the X-ray detector 4. The X-ray detector 4 outputs X-ray detection signals in accordance with intensity distribution of the X-rays. The A/D converter 8 converts analog X-ray detection signals outputted from the X-ray detector 4 into digital signals. An image with the subject M taken therein enables to be obtained in accordance with the digitized X-ray detection signals.

Step S02 First and Second Harmonic Removing Process

The peak frequency detector 25 detects a peak frequency of the first harmonic in the moiré pattern of the grid appearing in the image. The first and second harmonic remover 21 removes the first and second harmonics in the moiré pattern from the image in accordance with the peak frequency of the first harmonic to obtain a first and second harmonic removed image.

Step S03 Generation of Third Harmonic Extracting Filter

The third harmonic extracting-filter generating unit 29 calculates a peak frequency of the third harmonic in the moiré pattern in accordance with the peak frequency of the first harmonic to generate a third harmonic extracting filter used for extracting the third harmonic (FIG. 3).

Step S04 Extraction of Third Harmonic

The third harmonic extracting unit 31 extracts the third harmonic from the first and second harmonic removed image based on the third harmonic extracting filter (FIG. 5(*a*)). The third harmonic is extracted by performing filtering to every lateral pixel line in turn from the upper end of the first and second harmonic removed image using the third harmonic extracting filter.

Step S05 Vertical LPF Processing

The vertical LPF processor 33 performs one-dimensional low-pass filter (LPF) processing vertically along the fringes of the third harmonic (FIG. 5(*a*)) extracted by the third harmonic extracting unit 31. For instance, in the vertical LPF processing, a filter illustrated in FIG. 5(*b*), i.e., a filter having seventeen pixels consisting of a target pixel to be processed and upper eight and lower eight pixels across the target pixel is used, and the arithmetic mean of pixel values of the seventeen pixels is defined as a new pixel value of the target pixel. The processing is performed to each pixel, whereby the vertical pixels in the image are smoothed and an oblique pattern denoted by numeral n in FIG. 5(*a*) is removed. Consequently, an image of the third harmonic in the moiré pattern as illustrated in FIG. 4 enables to be obtained.

Step S06 Removing Third Harmonic (Subtraction)

As illustrated in FIG. 6, the third harmonic subtracting unit 35 subtracts the extracted third harmonic P2 from the first and second harmonic removed image P1 to obtain a third harmonic removed image P3.

Moreover, in parallel with Steps S03 to S06 to obtain the third harmonic removed image, Steps S13 to S15 are performed to calculate flatness in the first and second harmonic removed image, whereby flatness information is obtained.

Step S13 Amount of Intensity-Variation Calculation

The amount of intensity-variation calculating unit 41 subtracts an arithmetic mean value of the target pixel and the pixels therearound from the pixel value of the target pixel to obtain flatness information. That is, when the arithmetic mean value of the pixel values of 21×21 pixels including the target pixel is expressed by A and the pixel value of the target pixel is expressed by B as in FIG. 7, the amount of intensity-variation calculating unit 41 calculates an amount of intensity variation $C1=|B-A|$. Such processing is performed to every pixel, whereby flatness information is obtained as a new image.

Step S14 Normalization

The normalizing unit 43 performs normalization by dividing the amount of intensity variation of each pixel in the flatness information by the corresponding pixel value of the first and second harmonic removed image. That is, the amount of intensity variation C1 is divided by the pixel value B of the target pixel used for calculating the amount of intensity variation C1. The amount of intensity variation C2 after normalization is calculated by $$C2=|B-A|/B.$$

Step S15 Smoothing

The smoothing unit 45 performs smoothing by averaging the amount of intensity variation for every region into which the flatness information is divided by a plurality of pixels and by applying the arithmetic mean value to each pixel of the divided region. That is, the smoothing unit 45 performs average with 16×16 pixels, for example, for reduction into one pixel as illustrated in FIG. 8. Then, upon being returned to its original size, the averaged amount of intensity variation is applied to every pixel of the original 16×16 pixels.

Step S07 Output Selection

The output selecting unit 39 outputs the third harmonic removed image P3 in the flat region f of the flatness information P6, and outputs the first and second harmonic removed image P1 in the region out of the flat region f of the flatness information P6 as illustrated in FIG. 9. In this way, in the flat region f, an output selected image P7 with the third harmonic in the moiré pattern removed therefrom is obtained.

Step S08 Outputting and Storing

An image processor 9 performs other necessary processes to the output selected image P7 whose output is selected in step S07. Thereafter, the output selected image P7 is displayed on a display unit 11 and stored in the storing unit 13.

According to the X-ray diagnostic apparatus 1 in the embodiment of the present invention, the third harmonic extracting-filter generating unit 29 calculates the peak frequency of the third harmonic in the moiré pattern in accordance with the peak frequency of the first harmonic to generate the third harmonic extracting filter used for extracting the third harmonic. The third harmonic extracting unit 31 extracts the third harmonic from the first and second harmonic removed image based on the third harmonic extracting filter. The third harmonic subtracting unit 35 subtracts the extracted third harmonic from the first and second harmonic removed image to obtain the third harmonic removed image. Consequently, the third harmonic in the moiré pattern remaining in the first and second harmonic removed image enables to be removed.

Moreover, the X-ray diagnostic apparatus 1 further includes a flatness calculating unit 37 configured to calculate flatness in the first and second harmonic removed image to obtain flatness information; and an output selecting unit 39 configured to output the third harmonic removed image in the flat region of the flatness information and to output the first and second harmonic removed image in the region out of the flat region of the flatness information. The third harmonic of the moiré pattern is a frequency component with smaller spectrum intensity. Accordingly, the third harmonic is distinguishable in the flat region of the image with a little intensity variation and is not recognized in the region out of the flat region. Consequently, the output selecting unit 39 outputs the third harmonic removed image in the flat region of the flatness information acquired through calculating flatness by the flatness calculating unit 37, and outputs the first and second harmonic removed image in the region out of the flat region of the flatness information. That is, since third harmonic in the moiré pattern is distinguishable in the flat region of the first and second harmonic removed image, the third harmonic removed image is outputted only in the flat region under recognition of the flat region and the region other than the flat region. Accordingly, degradation in visibility of the image enables to be suppressed, and the third harmonic in the moiré pattern remaining in the moiré-pattern removed image enables to be removed.

Specifically, the image with less moiré pattern remaining therein enables to be obtained without degrading visibility in the region out of the flat region. Although the third harmonic in the moiré pattern having less intensity variation in the flat region is removed, influences of visibility degradation is difficult to be given relatively. In addition, an enhanced S/N ratio of the flat region enables to be achieved since the third harmonic in the moiré pattern of the flat region is removed.

Moreover, the amount of intensity-variation calculating unit 41 enables to obtain the flatness information representing the flatness of the first and second harmonic removed image by calculating the amount of intensity variation of the target pixel and the pixels therearound. In addition, the amount of intensity-variation calculating unit 41 enables to obtain the flatness information by subtracting the arithmetic mean value of the target pixel and the pixels therearound from the pixel value of the target pixel to calculate the amount of intensity variation.

Moreover, the normalizing unit 43 performs normalization by dividing the amount of intensity variation of each pixel in the flatness information by the corresponding pixel value of the first and second harmonic removed image. That is, a pixel with a higher pixel value is likely to have a larger amount of intensity variation, whereas a pixel with a lower pixel value is likely to have a smaller amount of intensity variation. The amount of intensity variation with the pixel of higher intensity and that with the pixel of lower intensity have the same amount of intensity variation, but differs from each other in its weight. Accordingly, dividing the amount of intensity variation of each pixel by the corresponding pixel value achieves comparison of the amount of intensity variation between the pixels of high and lower intensity on the same basis.

The smoothing unit 45 performs smoothing by averaging the amount of intensity variation for every region into which the flatness information is divided by a plurality of pixels (e.g., 16×16 pixels) to obtain an arithmetic mean value and by applying the arithmetic mean value to each pixel (16×16 pixels) in the divided region. The output selecting unit 39 enables to select output of the image not in pixel but in any region by smoothing. In addition, regions regarded as flat regions scattered out of the flat region enables to be processed as regions out of the flat region. Outputting the third harmonic removed image to the flat regions scattered out of the flat region may lead to visibility degradation.

The vertical LPF processor 33 performs one-dimensional LPF processing vertically along the fringes of the third harmonic extracted by the third harmonic extracting unit 31. An oblique pattern relative to the fringes of the third harmonic extracted in addition to the third harmonic of the moiré pattern enables to be removed.

This invention is not limited to the foregoing embodiments, but may be modified as follows.

(1) In the foregoing embodiment, the image processor 9 may include a controller formed by a CPU to execute programs and the like, and a storing unit formed by a storage medium such as a ROM or a RAM to store the programs. The storing unit may store programs about operations in Steps S01 to S08 and S13 to S15 and execute the programs by the controller. In this case, operations necessary for the programs is inputted by the input unit 12 and the output selected image P7 is displayed on the display unit 11.

(2) The foregoing embodiment is not limited to the image processor 9. Alternatively, the storing memory unit 13 may store programs about operations in Steps S01 to S08 and S13 to S15 and the main controller 10 may execute the programs. In this case, operations necessary for the programs is inputted by the input unit 12 and the output selected image P7 is displayed on the display unit 11. In addition, the programs about the operations may be executed by a personal computer connected to the X-ray diagnostic apparatus 1 via a network system such as a LAN.

The invention claimed is:

1. An X-ray diagnostic apparatus, comprising:
   an X-ray emitter configured to emit X-rays to a subject;
   an X-ray detector configured to detect X-rays transmitting through the subject; and
   a grid disposed on an X-ray incidence side of the X-ray detector to remove scattered X-rays, and configured to obtain an image in accordance with output from the X-ray detector,
   the X-ray diagnostic apparatus further comprising:
      a peak frequency detector configured to detect a peak frequency of a first harmonic in a moiré pattern of the grid appearing in the image;
      a first and second harmonic remover configured to remove the first harmonic and a second harmonic in the moiré pattern from the image in accordance with the peak frequency of the first harmonic to obtain a first and second harmonic removed image;
      a third harmonic extracting-filter generating unit configured to calculate a peak frequency of a third harmonic in the moiré pattern in accordance with the peak frequency of the first harmonic to generate a third harmonic extracting filter to extract the third harmonic;
      a third harmonic extracting unit configured to extract the third harmonic from the first and second harmonic removed image based on the third harmonic extracting filter;
      a third harmonic subtracting unit configured to subtract the extracted third harmonic from the first and second harmonic removed image to obtain a third harmonic removed image;
      a flatness calculating unit configured to calculate flatness in the first and second harmonic removed image to obtain flatness information; and
      an output selecting unit configured to output the third harmonic removed image within a flat region of the flatness information, and output the first and second harmonic removed image within a region out of the flat region of the flatness information.

2. The X-ray diagnostic apparatus according to claim 1, wherein
   the flatness calculating unit comprises an amount of intensity-variation calculating unit configured to calculate an amount of intensity variation between a target pixel to be processed and pixels therearound to obtain the flatness information.

3. The X-ray diagnostic apparatus according to claim 2, wherein
   the amount of intensity-variation calculating unit subtracts an arithmetic mean of the target pixel and the pixels therearound from a pixel value of the target pixel to obtain the flatness information.

4. The X-ray diagnostic apparatus according to claim 2, wherein
   the flatness calculating unit comprises a normalizing unit configured to divide an amount of intensity variation of each pixel in the flatness information by a corresponding pixel value in the first and second harmonic removed image to perform normalization.

5. The X-ray diagnostic apparatus according to claim 2, wherein
   the flatness calculating unit comprises a smoothing unit configured to average an amount of intensity variation for every region into which the flatness information is divided by a plurality of pixels and to perform smoothing by applying the arithmetic mean to each pixel of the divided region.

6. The X-ray diagnostic apparatus according to claim 1, further comprising:
   a low-pass filtering unit configured to perform one-dimensional low-pass filtering to an image of the third harmonic extracted by the third harmonic extracting unit along fringes of the third harmonic.

7. A non-transitory storage medium storing an X-ray diagnostic program for a computer to process an image taken via a grid configured to remove scattered X-rays, the program, when executed by the computer, causing the computer to perform:
   detecting a peak frequency of a first harmonic in a moiré pattern of the grid appearing in the image;
   removing the first harmonic and a second harmonic in the moiré pattern from the image in accordance with the peak frequency of the first harmonic to obtain a first and second harmonic removed image;
   calculating a peak frequency of a third harmonic in the moiré pattern in accordance with the peak frequency of the first harmonic to generate a third harmonic extracting filter to extract the third harmonic;
   extracting the third harmonic from the first and second harmonic removed image based on the third harmonic extracting filter;
   subtracting the third harmonic from the first and second harmonic removed image to obtain a third harmonic removed image;
   calculating flatness in the first and second harmonic removed image to obtain flatness information; and
   outputting the third harmonic removed image within a flat region of the flatness information, and outputting the first and second harmonic removed image within a region out of the flat region of the flatness information.

8. The X-ray diagnostic apparatus according to claim 3, wherein
   the flatness calculating unit comprises a normalizing unit configured to divide an amount of intensity variation of each pixel in the flatness information by a corresponding pixel value in the first and second harmonic removed image to perform normalization.

9. The X-ray diagnostic apparatus according to claim 3, wherein
   the flatness calculating unit comprises a smoothing unit configured to average an amount of intensity variation for every region into which the flatness information is divided by a plurality of pixels and to perform smoothing by applying the arithmetic mean to each pixel of the divided region.

10. The X-ray diagnostic apparatus according to claim 4, wherein
    the flatness calculating unit comprises a smoothing unit configured to average an amount of intensity variation for every region into which the flatness information is divided by a plurality of pixels and to perform smoothing by applying the arithmetic mean to each pixel of the divided region.

11. The X-ray diagnostic apparatus according to claim 8, wherein
    the flatness calculating unit comprises a smoothing unit configured to average an amount of intensity variation for every region into which the flatness information is divided by a plurality of pixels and to perform smoothing by applying the arithmetic mean to each pixel of the divided region.

12. The X-ray diagnostic apparatus according to claim 2, further comprising:
a low-pass filtering unit configured to perform one-dimensional low-pass filtering to an image of the third harmonic extracted by the third harmonic extracting unit along fringes of the third harmonic.

13. The X-ray diagnostic apparatus according to claim 3, further comprising:
a low-pass filtering unit configured to perform one-dimensional low-pass filtering to an image of the third harmonic extracted by the third harmonic extracting unit along fringes of the third harmonic.

14. The X-ray diagnostic apparatus according to claim 4, further comprising:
a low-pass filtering unit configured to perform one-dimensional low-pass filtering to an image of the third harmonic extracted by the third harmonic extracting unit along fringes of the third harmonic.

15. The X-ray diagnostic apparatus according to claim 5, further comprising:
a low-pass filtering unit configured to perform one-dimensional low-pass filtering to an image of the third harmonic extracted by the third harmonic extracting unit along fringes of the third harmonic.

16. The X-ray diagnostic apparatus according to claim 8, further comprising:
a low-pass filtering unit configured to perform one-dimensional low-pass filtering to an image of the third harmonic extracted by the third harmonic extracting unit along fringes of the third harmonic.

17. The X-ray diagnostic apparatus according to claim 6, further comprising:
a low-pass filtering unit configured to perform one-dimensional low-pass filtering to an image of the third harmonic extracted by the third harmonic extracting unit along fringes of the third harmonic.

18. The X-ray diagnostic apparatus according to claim 10, further comprising:
a low-pass filtering unit configured to perform one-dimensional low-pass filtering to an image of the third harmonic extracted by the third harmonic extracting unit along fringes of the third harmonic.

19. The X-ray diagnostic apparatus according to claim 11, further comprising:
a low-pass filtering unit configured to perform one-dimensional low-pass filtering to an image of the third harmonic extracted by the third harmonic extracting unit along fringes of the third harmonic.

20. An X-ray diagnostic apparatus, comprising:
an X-ray emitter configured to emit X-rays to a subject;
an X-ray detector configured to detect X-rays transmitting through the subject;
a grid disposed on an X-ray incidence side of the X-ray detector to remove scattered X-rays, and configured to obtain an image in accordance with output from the X-ray detector; and
a controller, wherein:
the controller includes a processor and a memory storing a program, and
the program, when executed by the processor, causes the controller to perform:
detecting a peak frequency of a first harmonic in a moiré pattern of the grid appearing in the image;
removing the first harmonic and a second harmonic in the moiré pattern from the image in accordance with the peak frequency of the first harmonic to obtain a first and second harmonic removed image;
calculating a peak frequency of a third harmonic in the moiré pattern in accordance with the peak frequency of the first harmonic to generate a third harmonic extracting filter to extract the third harmonic;
extracting the third harmonic from the first and second harmonic removed image based on the third harmonic extracting filter;
subtracting the third harmonic from the first and second harmonic removed image to obtain a third harmonic removed image;
calculating flatness in the first and second harmonic removed image to obtain flatness information; and
outputting the third harmonic removed image within a flat region of the flatness information, and outputting the first and second harmonic removed image within a region out of the flat region of the flatness information.

* * * * *